United States Patent [19]

Eifler et al.

[11] 4,159,234
[45] Jun. 26, 1979

[54] OXYGEN SENSOR

[75] Inventors: Raymond J. Eifler, Farmington Hills, Mich.; Donald C. Davis, Fostoria, Ohio

[73] Assignee: Bendix Autolite Corporation, Fostoria, Ohio

[21] Appl. No.: 879,031

[22] Filed: Feb. 21, 1978

[51] Int. Cl.² ............................................ G01N 27/46
[52] U.S. Cl. ................................................ 204/195 S
[58] Field of Search ............... 204/1 S, 195 S; 73/23; 324/71 R, 29; 123/119 E; 60/276; 23/254 E

[56] References Cited

U.S. PATENT DOCUMENTS

| | | | |
|---|---|---|---|
| 3,844,920 | 10/1974 | Burgett et al. | 204/195 S |
| 3,906,721 | 9/1975 | Micheli et al. | 60/276 |
| 4,057,477 | 11/1977 | Weyl et al. | 204/195 S |
| 4,098,653 | 7/1978 | Kita et al. | 204/1 T |

FOREIGN PATENT DOCUMENTS

| | | | |
|---|---|---|---|
| 2348505 | 4/1975 | Fed. Rep. of Germany | 204/195 S |
| 2351815 | 4/1975 | Fed. Rep. of Germany | 204/195 S |
| 2360818 | 6/1975 | Fed. Rep. of Germany | 204/195 S |

*Primary Examiner*—G. L. Kaplan
*Attorney, Agent, or Firm*—Raymond J. Eifler

[57] ABSTRACT

An oxygen sensor having a removably mounted shield (10) to protect the solid electrolyte tube (30) that extends from the sensor housing (20). In one embodiment of the invention the protective shield (10) includes a radially extending lip (12) that is snapped into an undercut (21) in the sensor housing (20).

8 Claims, 12 Drawing Figures

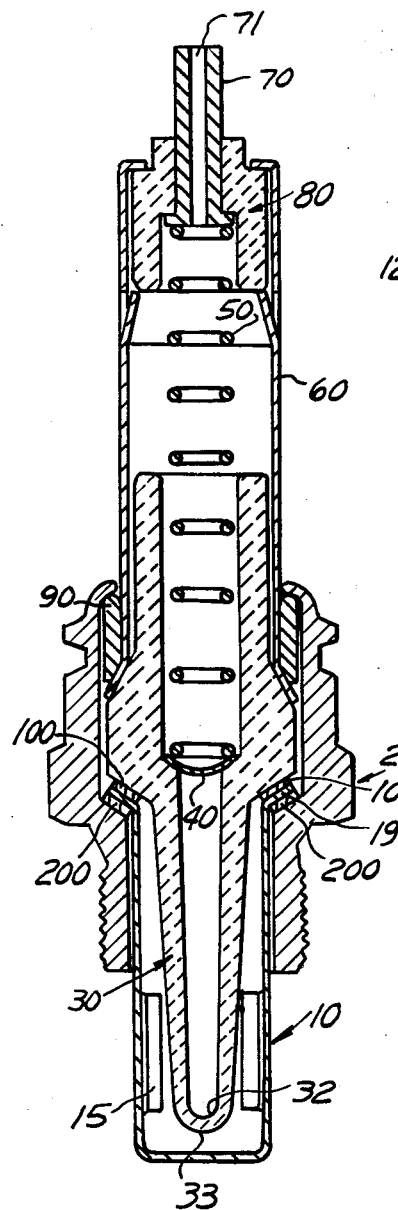

[4,159,234]

OXYGEN SENSOR

TECHNICAL FIELD

This invention relates to oxygen sensors of the type having a solid electrolyte. This invention is more particularly related to a shield which protects the solid electrolyte which extends from the housing of the sensor. The invention is also related to the hermetic seal between the solid electrolyte and the sensor housing.

BACKGROUND OF THE INVENTION

The exhaust gases of internal combustion engines include carbon monoxide, unburned or partially burned hydrocarbons and nitrogen-oxides which all contribute to air pollution. It is necessary to monitor the exhaust products emitted from automotive internal combustion engines in order to decrease air pollution by eliminating as many of the polluting compounds as possible. It is necessary to remove as much carbon monoxide and unburned hydrocarbons as possible from the exhaust of these engines by converting carbon monoxide and hydrocarbons into their highest oxidation state, that is, in the case of carbon monoxide, into carbon dioxide and in the case of hydrocarbons into water, and then to convert the nitrogen-oxides into elementary nitrogen.

Removing polluting components from the exhaust of internal combustion engines can be effected by conducting the exhaust gases at a temperature above 600° C. over a catalyst, so that the exhaust gases are subject to a post-combustion. The composition of the exhaust gases must be so arranged, however, that the relationship of air to fuel is approximately stoichiometric. Practically complete conversion to nonpolluting compounds is then possible. The stoichiometric relationship between air and fuel is characterized by a number $\lambda$ of unit ($\lambda = 1$). A lambda value equal to less than 1 means that no excess oxygen is present which exceeds the balance condition of the various respective actions which may take place; a lambda value greater than 1 means excess oxygen is present in the mixture; a lambda value exactly equal to 1 characterizes the state in which the exhaust gas changes from reducing to oxidizing.

Exhaust gases which are environmentally acceptable, as well as maximum use of fuel being supplied to an engine, better known as fuel efficiency, require the lambda value of the exhaust gases is approximately unity ($\lambda = 1$). Electro-chemical sensors when used to monitor and determine the oxygen content of an exhaust gas are exposed to the exhaust gases of an internal combustion engine. Control systems, responsive to output signals of the sensors, then react to adjust the relationship of air and fuel being supplied to the engine so that the air/fuel mixture will have a proper composition which, in turn, affects the exhaust gases emitted from the engine.

The oxygen sensors to which the present invention relates utilizes the principle of oxygen ion concentration and have ion conductive solid electrolytes. The solid electrolyte usually is in the shape of a tube, one end of which is closed; the closed end of the tube extending into the interior of an exhaust system so that the outside surface is exposed to exhaust gases. The outer surface, as well as the inner surface, of the electrolyte tube are coated, with an electron conductive layer, the outer surface including a catalyst. Each electron conductive layer, which may be in strip form, has a contact with which it is connected to an electrically conductive terminal portion. The terminal portions are usually so arranged that one terminal thereof is formed by the metal housing of the sensor which is secured to the exhaust system of an internal combustion engine. The other terminal is electrically connected to the inner postion of the oxygen sensor. The scientific principles upon which the solid electrolyte $O_2$ sensor operates may be found in U.S. Pat. No. Re. 28,792 entitled "Electrochemical Method for Separating $O_2$ From a Gas; Generating Electricity Measuring $O_2$ Partial Pressure; and Fuel Cell" issued Apr. 27, 1976. The solid electrolyte most generally used in such sensors is zirconium dioxide which is a relatively weak structural material. In applying such a sensor to a heated environment such as the automotive exhaust system, it has become apparent that thermal stressing of the zirconium dioxide sensor body is a significant source of sensor failure. Further, external forces applied to an unprotected zirconium dioxide sensor body can cause cracking of the sensor body and/or stresses in the hermetic seals which result in failures (short useful life). The prior art inventors recognizing this problem provided a protective shield to surround the solid electrolyte extending from the oxygen sensor. An example of one such protective shield is shown in U.S. Pat. No. 3,835,012 entitled "Protective Shield for Oxygen Sensor" issued Sept. 10, 1974. The shield shown in this patent is not removable and inspection of the electrolyte before installation is not possible. Further, the shield, which protects the solid electrolyte, extends into the sensor housing between the solid electrolyte body and the sensor housing which mean that a hermetic seal must then be made between the housing, the protective shield, the electrolyte, and appropriate sealing gaskets. Accordingly, any forces applied to the shield will be transmitted to the hermetic seal and in many instances cause a failure of the seal. This is obviously disadvantageous since the solid electrolyte sensor works on the principle of the different oxygen partial pressures on opposite sides (isolated from each other) of the electrolyte. Therefore, it is essential that the hermetic seal be intact to isolate the reference gas inside the solid electrolyte tube from the exhaust gas outside the tube.

Accordingly, prior art oxygen sensors do not have removable shields around the solid electrolyte to allow inspection of the electrolyte; and in some instances, the shield extended into the housing and became part of the hermetic seal between the solid electrolyte and the housing, thereby requiring a more complex hermetic seal, and, when the shield was part of the hermetic seal, forces applied to the shield (dropping, tapping, etc.) where transmitted to the hermetic seal, causing failure.

SUMMARY OF THE INVENTION

This invention provides a solid electrolyte sensing element with a removable and remountable protective shield so that the solid electrolyte may be inspected. The invention also removes the shield from being part of the hermetic seal between the solid electrolyte and the housing thereby making a less complex hermetic seal.

The invention is a solid electrolyte oxygen sensor characterized by having a removable shield (10) which protects the portion of a solid electrolyte (30) which projects from the sensor housing (20). The oxygen sensor is further characterized by the fact that the protective shield (10) does not form a part of the hermetic seal between the solid electrolyte and the housing (20).

One embodiment of the invention, used in combination with an electrochemical oxygen sensing element is of the type having a housing (20); with a front portion and a rear portion; a solid electrolyte tube (30) closed at one end thereof and mounted in the housing with said closed end projecting from the front portion of said housing (20), the solid electrolyte tube forming a solid ion conductive electrolyte concentration measuring element; first electrode means (32) inside of said electrolyte tube; means (71) formed in the housing providing access of ambient air to the inside of said solid electrolyte tube (30) to establish an oxygen reference potential; second electrode means (33) outside of said tube forming a catalyzing layer and connected to a terminal of said sensing element and adapted to be exposed to a gas, includes: an annular groove (21) in the inside of the front portion of the housing (20) and a protective tube (10) having an open end, an annular lip (12) extending radially outward from the open end of said tube and into the annular groove (21) in said housing (20), and at least two slots (11) spaced from each other and extending from the open end towards the other end of said protective tube, said slots (11) permitting said tube (10) to be compressed at said open end when a radially inward force is applied to the portions of the tube between the slots thereby decreasing the size of the protective tube (10) at the open end to permit removal of said annular lip (12) from the annular groove (21) in said housing (20) whereby said shield (10) may be removed from said housing (20) and, alternately, installed in said housing.

Accordingly, it is an object of this invention to provide an oxygen sensor with a removable and remountable shield which protects the solid electrolyte extending from the sensor.

It is another object of this invention to simplify the hermetic seal between the solid electrolyte and the housing of an oxygen sensor.

It is another object of this invention to increase the useful life of a solid electrolyte oxygen sensor.

It is a further object of the present invention to provide an improved electrochemical oxygen sensor.

The above and other objects and features of the invention will become apparent from the following detailed description taken in conjunction with the accompanying drawings and claims which form a part of this specification. Further, the use of numerals is for the purpose of clarification and is not intended to limit the invention to only the specific structure illustrated.

BRIEF DESCRIPTION OF THE DRAWINGS

FIG. 1 is a prior art oxygen sensor of the type having a solid electrolyte.

FIGS. 2, 3 and 4 are partial views of an oxygen sensor incorporating one of the features of this invention.

FIG. 5 is an alternate embodiment of a protective shield embodying one of the features of this invention.

FIGS. 6 and 7 are views of a protective shield illustrating another embodiment of the invention.

DETAILED DESCRIPTION OF THE DRAWINGS

Prior Art

Figure 12:
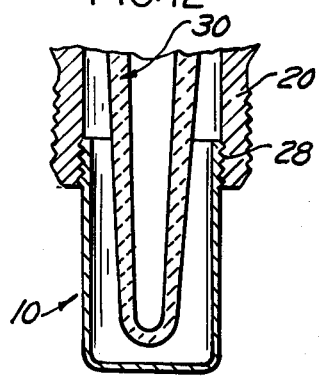
FIG. 12 is a partial diagrammatic view of another alternate embodiment of the invention.

Referring now to the drawings, FIG. 1 illustrates a prior art oxygen sensor. The oxygen sensor generally includes: a metal housing 20; a solid electrolyte 30 mounted within the housing and having a conductive coating 32 on the inside of the electrolyte and a conductive and catalytic coating 33 on the outside thereof, the inside coating forming an inside electrode 32 and the outside coating forming an outer electrode 33; a conducting member 40 contacting the inner electrode 32 of the electrolyte 30; a spring 50; an electrical contact 70 in contact with the spring 50 and the inside electrode 32 of the electrolyte 30, the electrical contact 70 having a passage 71 for the passage of ambient air to the inside of the electrolyte 30; an electrically insulating member 80 for spacing the terminal 70 from the outer tubular housing 60 which is in contact with the metal housing 20, and the outer electrode 33; and a spacer element 90 for retaining the outer tube 60 around the solid electrolyte. The hermetic seal between the solid electrolyte and the housing 20 includes the upper portion 19 of the protective shield 10 and two gaskets 100 and 200, preferably comprised of soft nickel. The shield 10 is generally made of stainless steel, which is very hard, and does not make a seal with the steel shell and the solid electrolyte without the use of an additional sealing gasket 200 or graphite packing. In some instances there are two nickel gaskets, one on each side of the upper portion 19 of the metal shield 10 to assure a good hermetic seal. This prior art figure of an oxygen sensor illustrates the non-removable aspect of the protective shield 10 as well as the complexity of the hermetic seal which is absolutely necessary for proper operation of the solid electrolyte sensor. Elimination of the oxygen portion 19 of the protective shield 10 from the hermetic seals permit removal of sealing gasket 200 and hence a less complex hermetic seal.

The Invention

The remaining FIGS. 2-11 illustrate different arrangements for the protective shield 10 in combination with the oxygen sensor which either allows the shield to be removed so the solid electrolyte can be inspected and/or removes any portion of the protective shield from being part of the hermetic seal between the solid electrolyte 30 and the outer housing 20.

FIG. 2 illustrates a protective housing 10 having a central bore 26, an annular lip 12 that is mounted in an annular undercut 21 in the sensor housing 20.

FIG. 3 shows a top view of the housing 10 which illustrates that the annular lip 12 in the protective shield 10 is formed into three segments separated one from the other by slots 11.

FIG. 4 illustrates a side view of the protective housing 10 shown in FIG. 3 and illustrates a preferred configuration of the slots 11. Although three slots are shown several slots can be used to facilitate the compression at the open end of the protective shield 10 to enable it to be compressed to a diameter small enough to be inserted into the bore (26, FIG. 2) in the sensor housing 20.

FIG. 5 illustrates an alternate embodiment of the invention. In this embodiment of the invention the protective shield 10 is not removable but is not part of the hermetic seal between the solid electrolyte 30 and the outer housing 20. In this embodiment the forward end portion 25 of the housing 20 has been rolled radially inwardly to captivate an outward extension 14 of the protective shield 10.

FIG. 6 illustrates a protective shield having a slot 11 and two radially outwardly extending pins 13.

FIG. 7 illustrates a bottom view of the protective shield shown in FIG. 6. In this embodiment of the invention, the protective shield 10 may be compressed at its open end so that the pins 13 may be snapped into one or more recesses (not shown) in the inside of a sensor housing.

Figure 8:
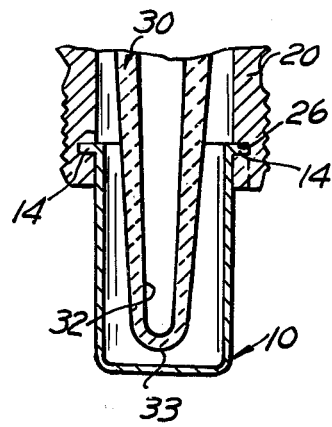
FIGS. 8, 9, 10 and 11 are views of another embodiment of the protective shield used in combination with the oxygen sensor.

FIG. 8 illustrates another embodiment of the invention where the protective shield 10 includes two radially outwardly extending pins 14 diametrically opposed one from the other. The pins 14 are mounted in grooves 26 in the sensor housing 20.

Figure 9:
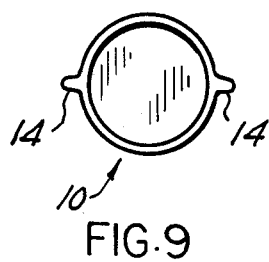

FIG. 9 illustrates a top view of the protective shield 10 illustrating the location of the two radially outwardly extending pins 14. Although only two pins 14 are shown there could be three or more pins 14.

Figure 10:
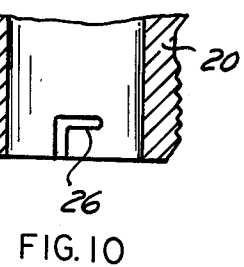

FIG. 10 illustrates a configuration of the groove 26 located in the inside wall of the sensor housing 20. As can be seen the groove 26 includes an axial portion and then a radially extending portion. This allows the pins 14 to be inserted into the axial portions and then rotated into the radial portion so that the protective shield 10 cannot be pulled off without being rotated.

The embodiment of the invention shown in FIGS. 8, 9 and 10 eliminates the protective shield from the hermetic seal. Also, in this embodiment it may not be necessary to have axial slots 11, as shown in FIG. 4, so long as there is a good pressure fit between the pins 14 and the inside of the groove 26 so that the protective shield is not easily rotated.

Figure 11:
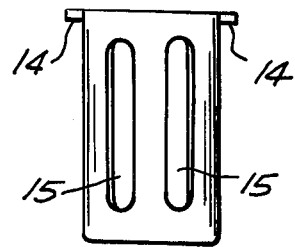

FIG. 11 illustrates a protective shield of the type shown in FIGS. 8 and 9. In the instance where there are no axial slots 11 as shown in FIG. 4, openings 15 must be provided in the shield to permit the passage of gas to the outside surface 33 of the solid electrolyte 30.

FIG. 12 illustrates another embodiment of the invention wherein the portective shield 10 is mounted to the sensor housing 20 by threads 28. Accordingly, by rotating the protective shield 10, the shield may be removed and, alternately, mounted to the sensor housing When inspection of the electrolyte is necessary or required, the protective shield may be removed and replaced.

While preferred embodiments of the invention have been disclosed, it may be apparent to others skilled in the art that changes may be made to the invention as set forth in the appended claims and, in some instances, certain features of the invention may be used to advantage without corresponding use of other features. For example, FIG. 5 illustrates an embodiment of the invention which does not provide a removable protective shield but does remove the protective shield 10 from the hermetic seal by attaching a protective shield in a novel manner.

Accordingly, it is intended that the illustrative and descriptive materials herein be used to illustrate the principles of the invention and not to limit the scope thereof.

Having described the invention, what is claimed is:

1. A sensor for sensing the oxygen concentration in a stream of gas and generating an electrical signal in response thereto, said sensor comprising:
   a tubular housing having a front portion and a rear portion, said front portion having an annular recess extending inwardly from the front end thereof and a forwardly extending outside portion;
   a zirconia body mounted to said housing, a portion of said zirconia body extending through and spaced from said forward portion of said housing, said body having an electrically conductive catalytic agent on a first surface adapted to be exposed to a gas and an electrically conductive material on a second surface adapted to be exposed to a reference gas;
   electrical conducting means connected to said surfaces on said body and extending therefrom through said housing for conducting the electrical signal generated in response to the difference in oxygen concentration adjacent said two surfaces; and
   a tubular shield having an interior surface spaced from the first surface of said zirconia body and enclosing said zirconia body, said shield having an open end, and an annular lip extending radially outwardly from said open end, said shield secured to said housing by said forwardly extending portion of said housing which has been rolled radially inward over the annular lip on said shield.

2. A sensor for sensing the oxygen concentration in a stream of gas and generating an electrical signal in response thereto, said sensor comprising:
   a tubular housing having a forward and a rear portion with said forward portion having an annular groove in the inside surface thereof;
   a zirconia body mounted to said housing, a portion of said zirconia body extending through and spaced from said forward portion of said housing, said body having an electrically conductive catalytic agent on a first surface adapted to be exposed to a gas and an electrically conductive material on a second surface adapted to be exposed to a reference gas;
   electrical conducting means connected to said surfaces on said body and extending therefrom through said housing for conducting the electrical signal generated in response to the difference in oxygen concentration adjacent said two surfaces; and
   a tubular shield having an interior surface spaced from the first surface of said zirconia body and enclosing said zirconia body, said shield having an open end, an annular lip extending radially outwardly from said open end and into the groove in said housing and at least two slots spaced from each other, each of said slots extending from the open end towards the other end of said shield, said slots permitting said shield to be compressed at said open end when a radially inward force is applied to the portion of the shield between the slots thereby decreasing the size of the shield at the open end and permitting removal of said annular lip from the groove in said housing whereby said shield may be removed from said housing, and, alternately, installed in said housing.

3. A sensor for sensing the oxygen concentration in a stream of gas and generating an electrical signal in response thereto, said sensor comprising:
   a tubular housing having a forward portion and a rear portion with said forward portion having threads on a portion of the surface thereof;

a zirconia body mounted to said housing, a portion of said zirconia body extending through and spaced from said forward portion of said housing, said body having an electrically conductive catalytic agent on a first surface adapted to be exposed to a gas and an electrically conductive material on a second surface adapted to be exposed to a reference gas;

electrical conducting means connected to said surfaces on said body and extending therefrom through said housing for conducting the electrical signal generated in response to the difference in oxygen concentration adjacent said two surfaces; and a tubular shield having an interior surface spaced from the first surface of said zirconia body and enclosing said zirconia body, said shield having an open end, and threads on a portion of said open end, said threads engaging the threads in said housing to retain said shield to said housing, said threads on said housing and said shield permitting said shield to be removed from said housing when the proper rotational force is applied to the shield, whereby said shield may be removed from said housing and, alternately, installed to said housing.

4. A sensor for sensing the oxygen concentration in a stream of gas and generating an electrical signal in response thereto, said sensor comprising:

a tubular housing having a forward portion and a rear portion, said forward portion having two spaced apart, axially extending and then radially extending grooves in the inside surface thereof;

a zirconia body mounted to said housing, a portion of said zirconia body extending through and spaced from said forward portion of said housing, said body having an electrically conductive catalytic agent on a first surface adapted to be exposed to a gas and an electrically conductive material on a second surface adapted to be exposed to a reference gas;

electrical conducting means connected to said surfaces on said body and extending therefrom through said housing for conducting the electrical signal generated in response to the difference in oxygen concentration adjacent said two surfaces; and a tubular shield having an interior surface spaced from the first surface of said zirconia body and enclosing said zirconia body, said shield having an open end and two, spaced apart, pins extending radially outwardly from the shield and into the radially extending portion of a respective groove in said housing, said radial pins permitting said shield to be removed from said housing when the proper rotational and axial force is applied to the shield whereby said shield may be removed from said housing and, alternately, installed in said housing.

5. In combination with an electrochemical oxygen sensing element used to determine the oxygen content in a gas wherein the sensing element is of the type having a housing with a front and rear portion and an annular groove in the inside of the front portion; a solid electrolyte tube closed at one end thereof and mounted in the housing and with said one end projecting from the front end of said housing, the solid electrolyte tube forming a solid ion conductive electrolyte oxygen concentration measuring element; first electrode means inside of said electrolyte tube; means formed in the housing providing access of ambient air to the inside of said solid electrolyte tube to establish an oxygen reference potential; second electrode means outside of said tube forming a catalyzing layer and connected to a terminal of said sensing element and adapted to be exposed to a gas; the improvement comprising:

a protective tube having an opening therein to permit the passage of gas to said electrolyte, said protective tube including an open end and an annular lip extending radially outwardly from said open end and into the annular groove in said housing, and at least two slots spaced from each other and extending from the open end towards the other end of said protective tube, said slots permitting said tube to be compressed at said open end when a radially inward force is applied to the portions of the tube between the slots, thereby decreasing the size of the protective tube at the open end to permit removal of said annular lip from the annular groove in said housing whereby said shield may be removed from said housing and, alternatively, installed in said housing.

6. In combination with an electrochemical oxygen sensing element used to determine the oxygen content in a gas wherein the sensing element is of the type having a housing with a front and rear portion and threads on the front portion; a solid electrolyte tube closed at one end thereof and mounted in the housing and with said one end projecting from the front end of said housing, the solid electrolyte tube forming a solid ion conductive electrolyte oxygen concentration measuring element; first electrode means inside of said electrolyte tube; means formed in the housing providing access of ambient air to the inside of said solid electrolyte tube to establish an oxygen reference potential; second electrode means outside of said tube forming a catalyzing layer and connected to a terminal of said sensing element and adapted to be exposed to a gas; the improvement comprising:

a protective tube having an opening therein to permit the passage of gas to said electrolyte, said protective tube including an open end and threads on the portion of said protective tube having said open end, said threads engaging the threads on said housing to retain said protective tube to said housing, said threads on said housing and said protective tube permitting said protective tube to be removed from said housing when proper rotational force is applied to the protective tube, whereby said shield may be removed from said housing.

7. In combination with an electrochemical oxygen sensing element used to determine the oxygen content in a gas wherein the sensing element is of the type having a housing with a front and rear portion and two spaced apart axially extending and then radially extending grooves in the forward portion of said housing; a solid electrolyte tube closed at one end thereof and mounted in the housing and with said one end projecting from the front end of said housing, the solid electrolyte tube forming a solid ion conductive electrolyte oxygen concentration measuring element; first electrode means inside of said electrolyte tube; means formed in the housing providing access of ambient air to the inside of said solid electrolyte tube to establish an oxygen reference potential; second electrode means outside of said tube forming a catalyzing layer and connected to a terminal of said sensing element and adapted to be exposed to a gas; the improvement comprising:

a protective tube having an opening therein to permit the passage of gas to said electrolyte, said protective tube including an open end and two spaced apart pins extending radially from the protective tube and into the radially extending portion of a respective groove in said housing, said radial pins permitting said protective tube to be removed from said housing when the proper rotational and axial force is applied to the tube, whereby said tube may be removed from said housing.

8. In combination with an electrochemical oxygen sensing element used to determine the oxygen content in a gas wherein the sensing element is of the type having a housing with a front and rear portion and two recesses, spaced from each other, in the forward portion of said housing; a solid electrolyte tube closed at one end thereof and mounted in the housing and with said one end projecting from the front end of said housing, the solid electrolyte tube forming a solid ion conductive electrolyte oxygen concentration measuring element; first electrode means inside of said electrolyte tube; means formed in the housing providing access of ambient air to the inside of said solid electrolyte tube to establish an oxygen reference potential; second electrode means outside of said tube forming a catalyzing layer and connected to a terminal of said sensing element and adapted to be exposed to a gas; the improvement comprising:

a protective tube having an opening therein to permit the passage of gas to said electrolyte, said protective tube including an open end, two spaced apart pins extending radially from the protective tube and into a respective recess in said housing, and at least one slot extending from the open end towards the other end of said protective tube, said slot permitting said tube to be compressed at said open end when a radially inward force is applied to the open end portion of the protective tube, thereby decreasing the size of the protective tube at the open end to permit removal of said pins from the recesses in said housing whereby said shield may be removed from said housing and, alternately, installed in said housing.

* * * * *